United States Patent [19]

Bither et al.

[11] Patent Number: 4,885,204

[45] Date of Patent: Dec. 5, 1989

[54] ABSORBENT PRODUCT WITH HYDROPHOBIC ACQUISITION LAYER

[75] Inventors: Peter G. Bither, Wilmington, Del.; Berne F. Ellers, Orkelljunga, Sweden; Edward J. Engle, III, Hockessin, Del.

[73] Assignee: Hercules Incorporated, Wilmington, Del.

[21] Appl. No.: 238,686

[22] Filed: Aug. 31, 1988

[30] Foreign Application Priority Data

Sep. 18, 1987 [GB] United Kingdom ............... 8722004

[51] Int. Cl.$^4$ .......................... A61F 13/16; B32B 7/00
[52] U.S. Cl. .................................... 428/284; 428/286; 428/288; 428/913; 604/378; 604/381
[58] Field of Search ............... 428/284, 286, 288, 913; 604/378, 367, 375, 381

[56] References Cited

U.S. PATENT DOCUMENTS

| 4,324,247 | 4/1982 | Aziz | 604/378 |
| 4,338,371 | 7/1982 | Dawn et al. | 604/378 |
| 4,590,114 | 5/1986 | Holtman | 428/171 |
| 4,673,402 | 6/1987 | Weisman et al. | 604/378 |
| 4,798,603 | 1/1989 | Meyer et al. | 604/378 |

FOREIGN PATENT DOCUMENTS

| 40447 | 11/1981 | European Pat. Off. |
| 0165807 | 12/1985 | European Pat. Off. |
| 1160625 | 8/1969 | United Kingdom |

Primary Examiner—Marion C. McCamish
Assistant Examiner—Nizar M. Ibrahim
Attorney, Agent, or Firm—Joanne W. Patterson

[57] ABSTRACT

Disclosed is a laminated structure for use in an absorbent product comprising a hydrophobic acquisition layer adjacent to a fluid permeable top sheet, and an absorbent layer. The hydrophobic layer comprises a thermally consolidated blend of 5% to 35% of thermally bondable hydrophobic fibers and 65% to 95% wood fluff pulp.

8 Claims, No Drawings

ABSORBENT PRODUCT WITH HYDROPHOBIC ACQUISITION LAYER

FIELD OF THE INVENTION

This invention relates to an improved construction for an absorbent product. This invention especially relates to an absorbent product having a hydrophobic acquisition layer adjacent to a fluid permeable top sheet.

BACKGROUND OF THE INVENTION

Most currently available absorbent products such as baby diapers, feminine hygiene products and adult incontinence pads have an absorbent layer adjacent to a liquid permeable top sheet referred to as cover stock. The cover stock holds the absorbent core in place and also acts as a one-way barrier that permits the flow of body fluid into the absorbent core, but inhibits its flow back towards the skin.

The time required for liquid to penetrate through the cover stock is called the strike-through time. When strike-through is long, body fluids spread over the cover stock and reach the edges of the product quickly. In this situation, more of the wearer's skin is exposed to the fluid and the fluid is more likely to leak from the absorbent product. Shorter strike-through times are likely to result in a product with less leakage and a softer, drier feel to the wearer.

Rewet is the amount of fluid that flows from the absorbent core back through the cover stock to the wearer's skin, particularly upon application of pressure. Users of products having improved rewet are less likely to experience skin irritation or bed sores.

An absorbent product with a shorter strike-through time and less rewet than currently available products would be desirable.

SUMMARY OF THE INVENTION

It has now been found that an absorbent product that includes a hydrophobic acquisition layer next to the cover stock has a short strike-through time and low rewet. The laminated structure of this invention, suitable for use as a component of an absorbent product, comprises a hydrophobic acquisition layer adjacent to a fluid permeable top sheet, and an absorbent layer, said hydrophobic layer comprising a thermally consolidated blend of from about 65% to about 95% wood fluff pulp and from about 5% to about 35% of a thermally bondable hydrophobic fiber, based on the weight of the blend.

DETAILED DESCRIPTION OF THE INVENTION

The laminated structure of this invention comprises a fluid permeable top sheet, a hydrophobic acquisition layer adjacent to and in intimate contact with the top sheet and an absorbent layer. A nonwoven cellulosic tissue can be positioned between the hydrophobic acquisition layer and the absorbent layer.

The amount of hydrophobic fiber used in the blend of wood fluff pulp and thermally bondable hydrophobic fiber in the acquisition layer is from about 5% to about 35%, preferably from about 20% to about 30% of the fiber, based on the total weight of the acquisition layer. The hydrophobic fiber can be a cut staple fiber such as fibers of polypropylene or polyethylene or copolymers thereof, or polyolefin pulp such as polypropylene or polyethylene pulp. Polyolefin pulp is preferred. Since the pores produced by melting of the polyolefin fibers during thermal consolidation of the blend develop a more hydrophobic surface and increase in size compared to the unconsolidated blend, the wicking of absorbed liquid back to the top sheet is minimized and rewet is lower. The greater the concentration of synthetic pulp, the larger the pores and the more hydrophobic the surface of the pores.

Polyolefin pulps are well known in the art. For example, see "Pulp, Synthetic," Kirk-Othmer, *Encyclopedia of Chemical Technology*, 3rd Ed. (New York: 1982), Vol. 19, pp. 420–435. The pulps are very fine, highly branched, discontinuous fibrils made from thermoplastic polymers. Their visual appearance and dimensions closely resemble those of wood pulp.

Representative of the polymers from which the polyolefin pulps are made are polyethylene, polypropylene, copolymers of ethylene and propylene, copolymers of propylene and other 1-olefins such as 1-butene, 4-methylpentene-1 and 1-hexene. The polyolefin pulps can be composed solely of one of these polymers, or they can be composed of mixtures of two or more of the polymers. The preferred polyolefin pulps are those prepared from polyethylene or polypropylene.

Poly(vinyl alcohol) (PVA) can be used to treat the polyolefin pulp to make it more dispersible in water during sheet formation. If PVA is used, from about 0.2% to about 2% is applied, based on the weight of the polyolefin pulp. Such PVA-treated polyolefin pulps are available commercially, for example, PULPEX ®E-D and P-AD polyolefin pulps, supplied by Hercules Incorporated. PVA-treated polyolefin pulp is hydrophobic after thermal consolidation.

The wood fluff pulp in the hydrophobic acquisition layer can be a chemical or mechanical pulp derived from either softwoods or hardwoods. The amount of wood fluff pulp used is from about 65% to about 95%, preferably 78% to 80%, based on the total weight of the acquisition layer. The fluff pulp can be made more hydrophobic by treating with from about 0.1% to about 0.5% of ketene dimer. About 0.25%, based on the weight of the wood fluff pulp, is preferred. The ketene dimer can be applied, for example, by spraying it in the form of an aqueous dispersion onto the moving web of the hydrophobic fiber/wood fluff pulp blend before the blend is thermally consolidated.

The ketene dimers that can be used for treating the wood fluff pulp are dimers having the formula $[RCH=C=O]_2$ where R is a hydrocarbon radical, such as alkyl having at least 8 carbon atoms, cycloalkyl having at least 6 carbon atoms, aryl, aralkyl, and alkaryl. In naming ketene dimers, the radical "R" is named followed by "ketene dimer." Thus phenyl ketene dimer is:

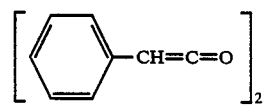

and decyl ketene dimer is: $[C_{10}H_{21}-CH=C=O]_2$. Representative ketene dimers that can be used in the process of the instant invention include octyl, decyl, dodecyl, tetradecyl, hexadecyl, octadecyl, eicosyl, docosyl, tetracosyl, phenyl, benzyl, beta-naphthyl and cyclohexyl ketene dimers, as well as the ketene dimers prepared from palmitoleic acid, oleic acid, ricinoleic acid, linoleic acid, and linolenic acid. Ketene dimers prepared from naturally occurring mixtures of fatty acids, such as those mixtures found in coconut oil, palm kernel oil, palm oil, olive oil, peanut oil, and rape oil as well as mixtures of any of the above-named fatty acids with each other can also be used.

The fluff pulp and the hydrophobic fiber are blended by any of the known blending methods. Such methods include the preparation of a pulp sheet by conventional paper-making procedures or by conventional dry blending methods.

After blending, the spurted polyolefin and wood pulps are fluffed and formed into a fluff pad by conventional methods such as hammermilling or air forming. The polyolefin pulp and wood pulp can also be fluffed prior to blending. The order of fluffing and blending is not critical.

The hydrophobic fiber/wood fluff pulp blend is consolidated by heating at a temperature and for a time sufficient to raise the temperature of the blend to above the melting point of the hydrophobic fiber. For example, the melting point of polyethylene pulp is 132° C., while the melting point of polypropylene pulp is 165° C. Methods used to fuse the hydrophobic fiber are known in the art and include the use of calenders, infrared heaters and pull-through dryers. Exact conditions, which will be readily ascertained by one skilled in the art, must be determined for the specific blend being used. The time, which is also readily ascertained by one skilled in the art, generally ranges from 1 second to about 10 minutes.

After thermal consolidation the density of the hydrophobic acquisition layer is controlled to between 0.03 and 0.12 g/cc, for example, by passing through a calender. A density of 0.04 to about 0.06 g/cc is preferred.

The average pore size of the hydrophobic acquisition layer after thermal consolidation is greater than the average pore size of the absorbent layer.

The contact angle of the hydrophobic acquisition layer is greater than the contact angle of the cover stock material or the absorbent layer. Contact angle is defined as the angle between the surface of a drop of fluid and the substrate with which it is in contact. The higher the contact angle, the poorer the wettability of the substrate by the fluid. A substrate is considered to be hydrophobic if the contact angle is close to or greater than 90° and hydrophilic if the contact angle is substantially less than 90°.

The effectiveness of the hydrophobic layer depends upon the existence of a driving force sufficient to pull the fluid through the hydrophobic layer. This driving force can be provided, for example, by the use of a layer of nonwoven cellulosic material, hereafter referred to as tissue, between the hydrophobic layer and the absorbent layer, or by the presence of a "superabsorbent" in the absorbent layer. In the case of the tissue, the driving force is provided by the tendency of a fluid to spontaneously flow from a layer containing large pores (i.e., the hydrophobic layer) to an adjacent layer having smaller pores (i.e., the tissue layer). In the case of an absorbent layer containing "superabsorbent", the driving force is provided by the strong affinity of the "superabsorbent" for liquids.

The tissue is a fine pore, high density cellulosic material commonly used in the manufacture of facial tissues, toweling and napkins. The cellulosic material is wood pulp made by either the sulfite or the sulate process. The tissue is made on a dry creped wadding machine where the material is creped to impart elongation, typically 12% to 20% in the machine direction. This type of material generally does not contain any chemical additives such as debonding agents or surfactants.

The "superabsorbent" that can be used in the absorbent layer is a water-swellable, water-insoluble polymeric absorbent material and includes cross-linked polyacrylates, cross-linked sulfonated polystyrenes, cross-linked poly(alkylene oxides) and graft copolymers of water-insoluble polysaccharides such as starch and cellulose. The polymeric absorbent is normally in the form of a fiber or powder. Such materials are well known in the art, for example, as described in U.S. Pat. Nos. 3,669,107 (Harper et al.), 3,670,731 (Harmon) and 4,235,237 (Mesek et al.).

The type of cover stock used is not critical to this invention. Currently available materials are made of fibers including rayon, polyester, polypropylene and wood pulp, which are formed into different web or sheet structures by means of various forming and bonding techniques. The finished products include fabrics that are carded/latex bonded, carded/thermal bonded, spunbonded, wet-laid and air-laid/bonded, wet formed, spunlaced and knitted. These materials are available in varying ranges of weight per unit area, thickness, dry and wet tensile strength and stiffness. The fibers from which the cover stock is produced are typically surface-treated to render them hydrophilic.

The composition of the absorbent layer is also not critical to the present invention. The absorbent layer is usually composed mainly of wood fluff pulp, but may additionally contain peat moss, creped wadding, melt blown polyolefin fiber, cut staple fibers of polyolefin, polyester or various nonwoven scrims of cover stock-like material. As mentioned previously, a "superabsorbent" may also be present in the absorbent layer.

The TEFO rewet test used in the following examples was developed by the Institute for Textile Research (Sweden) and is conducted as follows. An absorbent product that has a cover stock layer is placed in the TEFO absorption tester. 1.0% NaCl solution at 8.3 times the sample weight is added under a load of 100 Pa. After two minutes, the sample is removed from the tester and the cover stock is removed. The cover stock is placed on a steel plate and covered with filter paper. A 20 g weight is placed on the filter paper for two minutes, after which the filter paper is removed and weighed.

The strike-through time is defined as the time in seconds required for 5 ml of 1.0% saline solution to be completely absorbed by the sample.

EXAMPLE 1

RAYFLOC J bleached kraft pulp supplied by ITT Rayonier, Inc. is fed to a hammermill where it is combined with wet fluffed PULPEX ®E-D polyolefin pulp (Hercules Incorporated). The combination of polyolefin pulp and wood pulp is then metered via a forming head onto a tissue having a basis weight of 20 gsm (Seraccius Paper Company, Finland) at a concentration of 30 to 130 grams per square meter (gsm).

The web is then passed through a three section drying tunnel at temperatures of 50° C. (zone 1), 150° C. (zone 2) and 150° C. (zone 3). The density of the web is controlled to about 0.05 g/cc by passing through a calender. The web is stabilized by passing mill air at ambient temperature (23° C.) through the web in a cooler. The composition of the web is 20% PUL- PEX®E-D polyolefin pulp and 80% wood fluff pulp and the basis weight of the thermally bonded hydrophobic layer is 50 gsm.

The commercial products described below are tested for strike-through time and rewet. The combination of the hydrophobic acquisition layer and tissue prepared as described above is then slipped between the cover stock and the absorbent core of the same commercial products and the tests are repeated. The results are given in Table 1. In the table, the commercial products are designated as "standard" and the combination of commercial product plus the hydrophobic acquisition layer of this invention is designated as "new". The commercial products tested are:

(1) Feminine napkin. The product contains about 14 g of fluff pulp and tissue with a 17 gsm carded thermally bonded polypropylene cover stock and a low density polyethylene barrier film backing.

(2) Baby diaper. The product contains 37.5 g fluff pulp, 3.5 g tissue and 4.6 g superabsorbent, and has a 24 gsm carded thermally bonded polypropylene top sheet.

(3) Incontinence pad. The core contains 30% SOL-SORB 86 superabsorbent, 18% PULPEXR E-338 polyolefin pulp (Hercules Incorporated) and 52% RAY-FLOC J (ITT Rayonier, Inc.). Two plies with a basis weight of 355 gsm were air-laid on a 20 gsm tissue. The cover stock is thermally bonded polypropylene with a basis weight of 16 gsm.

(4) Incontinence brief. The product contains approximately 28% melt blown polypropylene fiber in two layers blended with wood fluff pulp in the top ply, and wood fluff pulp plus superabsorbent powder in the bottom ply next to a barrier film. The top sheet is spunbonded polypropylene.

TABLE 1

|  | Strike-Through (sec) | | Rewet (g) | |
| --- | --- | --- | --- | --- |
|  | Standard | New | Standard | New |
| Feminine Napkin | 5.0 | 4.4 | 0.130 | 0.041 |
| Baby Diaper | 5.8 | 3.9 | 0.068 | 0.052 |
| Incontinence Pad | 4.6 | 3.8 | 0.036 | 0.030 |
| Incontinence Brief | 4.0 | 2.7 | 0.600 | 0.220 |

EXAMPLE 2

A hydrophobic acquisition layer is prepared as described in Example 1, except that after metering the blend of PULPEX®E-D polyolefin pulp and RAY-FLOC J onto the tissue, an emulsion of AQUA-PEL®360X alkylketene dimer emulsion (Hercules Kemiska AB-Gothenberg, Sweden) is diluted 3:1 with water and sprayed onto the moving web before passing through the drying tunnel. The amount of ketene dimer retained is about 0.2%, based on the weight of the wood fluff pulp.

What we claim and desire to protect by letters patent is:

1. A laminated structure suitable for use as a component of an absorbent product comprising a hydrophobic acquisition layer adjacent to a fluid permeable top sheet, and an absorbent layer, said hydrophobic layer comprising a thermally consoldated blend of from about 5% to about 35% of a thermally bondable hydrophobic fiber selected from hydrophobic staple fibers and polyolefin pulps, and from about 65% to about 95% of wood fluff pump, based on the weight of the blend.

2. The structure of claim 1 wherein the hydrophobic fiber is polyethylene pulp or polypropylene pulp.

3. The structure of claim 2 which also comprises a layer of nonwoven cellulosic tissue positioned between the hydrophobic acquisition layer and the absorbent layer.

4. The structure of claim 1 which also comprises a layer of nonwoven cellulosic tissue positioned between the hydrophobic acquisition layer and the absorbent layer.

5. The structure of claim 4 wherein the absorbent layer contains a water-swellable, water-insoluble polymeric absorbent material.

6. The structure of claim 1 wherein the absorbent layer contains a water-swellable, water-insoluble polymeric absorbent material.

7. The structure of claim 1 wherein the wood fluff pulp in the hydrophobic acquisition layer is treated with 0.1% to 0.5% ketene dimer, based on the weight of the wood fluff pulp.

8. The structure of claim 1 wherein the density of the hydrophobic acquisition layer is from about 0.03 to about 0.12 g/cc.

* * * * *

UNITED STATES PATENT AND TRADEMARK OFFICE
CERTIFICATE OF CORRECTION

PATENT NO. : 4,885,204
DATED : December 5, 1989
INVENTOR(S) : Bither, Ellers & Engle It is certified that error appears in the above-identified patent and that said Letters Patent is hereby corrected as shown below:

Column 3, line 67 " sulate "

should read -- sulfate --

Column 5, line 24 " PULPEXR "

should read -- PULPEX$^R$ --

Column 6, line 16 and 18 " absorbant "

should read -- absorbent --

Column 6, line 19 " consoldated "

should read -- consolidated --

Column 6, line 23 " pump "

should read -- pulp --

Signed and Sealed this

Twenty-second Day of January, 1991

*Attest:*

HARRY F. MANBECK, JR.

*Attesting Officer*         *Commissioner of Patents and Trademarks*